(12) United States Patent
Feine

(10) Patent No.: US 7,766,656 B1
(45) Date of Patent: Aug. 3, 2010

(54) DENTAL DELIVERY DEVICE

(75) Inventor: James Feine, Bellaire, TX (US)

(73) Assignee: Hu-Friedy Mfg. Co., Inc., Chicago, IL (US)

( * ) Notice: Subject to any disclaimer, the term of this patent is extended or adjusted under 35 U.S.C. 154(b) by 815 days.

(21) Appl. No.: 11/162,069

(22) Filed: Aug. 26, 2005

Related U.S. Application Data

(60) Provisional application No. 60/604,967, filed on Aug. 27, 2004.

(51) Int. Cl.
*A61C 5/04* (2006.01)
(52) U.S. Cl. ........................................ 433/89
(58) Field of Classification Search ............... 433/80, 433/89, 90, 215, 88, 86, 119; 222/566–574, 222/196–203; 128/200.16; 601/162–163; 604/22
See application file for complete search history.

(56) References Cited

U.S. PATENT DOCUMENTS

| | | | | |
|---|---|---|---|---|
| 3,809,977 A | * | 5/1974 | Balamuth et al. | 433/119 |
| 3,827,147 A | * | 8/1974 | Condon | 433/90 |
| 4,540,365 A | * | 9/1985 | Nelson et al. | 433/88 |
| 5,033,650 A | * | 7/1991 | Colin et al. | 433/90 |
| 5,370,534 A | * | 12/1994 | Wolf et al. | 433/80 |
| 5,743,431 A | * | 4/1998 | Brattesani | 433/90 |
| 5,927,977 A | * | 7/1999 | Sale et al. | 433/86 |
| 6,648,641 B1 | * | 11/2003 | Viltro et al. | 433/80 |
| 2004/0186415 A1 | * | 9/2004 | Burbank et al. | 604/6.16 |
| 2005/0233280 A1 | * | 10/2005 | Hamman | 433/88 |

* cited by examiner

*Primary Examiner*—Cris L Rodriguez
*Assistant Examiner*—Heidi M Eide
(74) *Attorney, Agent, or Firm*—Marshall, Gerstein & Borun LLP

(57) ABSTRACT

A single use cartridge 10 is disclosed for dispensing a medicament or other substance for dental, medical, or veterinarian applications. A motive fluid can contact the medicament to mix and dispense from reservoir 12, or the motive fluid can act on a plunger 21 to dispense the medicament. A handpiece 15 can sealably connect the cartridge 10 to a source of the motive fluid. The cartridge 10 can be easily replaced to facilitate the use of multiple cartridges with a single handpiece 15. An ultrasonic cleaning element 30 with a channel for fluid flow can be used in a handpiece 25 with a single use medicament cartridge 28 to dispense medicament during ultrasonic dental procedures. A cartridge 72 can contain a mixing element 70 to mix the motive fluid and abrasive particles for tooth surface polishing.

5 Claims, 4 Drawing Sheets

DENTAL DELIVERY DEVICE

CROSS REFERENCE TO RELATED APPLICATION

This application claims the benefit of my earlier application U.S. Ser. No. 60/604,967 filed Aug. 27, 2004.

FIELD OF THE INVENTION

This invention relates to dental delivery devices, more particularly, to a single use medicament delivery device with a replaceable cartridge. The invention addresses such current issues as infection control, medicament dispensing, dental scaling, polishing, and surface abrading while maintaining ease of use, size, and portability.

BACKGROUND OF THE INVENTION

Dental equipment and techniques have evolved over the past decades of use. New concerns such as infection control and sterility of equipment and materials have become increasingly important, both to the patient and to the dental professional. Dental professionals require equipment for dispensing many substances including air, water, medicament, surface abrading materials, impression material, sealants, coatings, anesthetics, fluoride containing gel or solution, etc.

Most dental equipment is required to be sterilized which consumes time and labor. Many different patients may receive treatment from one dental professional in the same day, and there is not usually time to sterilize the equipment between procedures, so the practitioner must have several of the same type of tool ready for use. Different dental equipment may be used during the same procedure. Often, one set of equipment may be used for one type of procedure, whereas a similar set may used for another. Furthermore, in some offices, there may be several practitioners, each having his or her own preference for types of equipment for particular procedures. Additionally, a medicament can be applied during the procedures which can necessitate a separate medicament dispenser for each differing medicament. Each device requires time, labor, and capital to own, operate, and sterilize.

Dental dispensing devices can require a gas, liquid, or electrical means for operation, which can lead to a complicated supply system. In addition to the expense, having a multitude of supply systems can lead to an unsafe environment due to the close proximity to the patient and dental professional. Some medicaments require mixing with a gas, a liquid, or both, which can require different connections to the office air and water supply creating even more complications.

Some current tooth polishing systems in use that provide baking soda polishing functions are charged with powder in a reservoir in the base unit in an amount for multiple uses or procedures. This powder can absorb moisture from the surroundings and clog the orifices and tubing. Operators of these units can have difficulties in cleaning the powder reservoirs and keeping them dry, and removing, cleaning, and disinfecting their assemblies. Moreover, the base reservoir does not facilitate easy change of the polishing compound for different patients who require a different type or would like a different flavor.

Ultrasonic dental equipment is commonly used in hygienics, periodontal and other dental procedures. This requires additional equipment to be purchased and sterilized for each patient if a medicament is used with the ultrasonic scaler treatment, in addition to the time wasted by the dental professional setting up and switching equipment.

SUMMARY OF THE INVENTION

The present invention is directed to a single-use cartridge for delivering a unit dose of medicament in dental procedures, for example. The medicament can be dispensed from the cartridge using a sterilizable or disposable handpiece and a motive fluid such as air or water. The single-use cartridge can be used to deliver medicament per se, to provide a tooth surface polishing spray of water, air and abradant, or to deliver medicament in an ultrasonic dental procedure.

In one embodiment, the present invention provides a delivery device for medicament. The delivery device includes a cartridge having a reservoir containing a unit dose of medicament. A tip is operably connected at a distal end of the cartridge. A port is provided in the cartridge for removably connecting the cartridge to a source of a motive fluid to displace medicament from the reservoir through a channel in the tip.

In another embodiment, a delivery device for medicament includes a cartridge housing a reservoir containing a unit dose of medicament, and a handpiece with a cavity removably receiving the cartridge. A tip is operably connected at a distal end of the cartridge to project through an opening at a distal end of the handpiece. A source of a first motive fluid is in communication with a first passage in the handpiece, and a first port in the cartridge can connect the first passage to the reservoir for supplying the first motive fluid to displace medicament from the reservoir through a channel in the tip. The tip can be removably connected to the cartridge. The handpiece can be autoclavable. The medicament can be a fluoride gel, for example. The reservoir can further contain a plunger which is drivable by the first motive fluid against the medicament to dispense medicament. In another embodiment, cartridge can have a first port in fluid communication with the medicament in the reservoir. The medicament can be concentrated and the medicament displaced through the channel can be mixed with the first motive fluid.

In another embodiment a source of a second fluid is in communication with a second passage in the handpiece and a second port in the handpiece for connection to the second passage.

In another embodiment, the cartridge can include a second port for supplying the second fluid to the reservoir from the second handpiece port. One of the first and second cartridge ports can be selectively blocked and the other of the first and second cartridge ports can be open. The first and second ports can have different sizes to align the cartridge in the handpiece.

In another embodiment, the single use cartridge can include a flow channel through the cartridge for the second fluid to flow from the second port to the tip separate from the reservoir, and a mixing element can introduce a mixture of the first fluid and medicament from the reservoir into the channel. This first motive fluid can comprise a gas such as air and the second motive fluid can comprise a liquid such as water.

In another embodiment, the mixing element can comprise outer and inner concentric tubes with a flow path for supplying air and medicament from the reservoir to the inner tube or comprise a nozzle.

In another embodiment, the present invention can include an ultrasonic element disposed between the distal end of the cartridge and the tip with a flow path in the ultrasonic element in fluid communication with the reservoir and the channel in the tip. The ultrasonic element can be powered by a circuit through the cartridge which connects the handpiece to an electrical connection in the ultrasonic element. The cartridge can be essentially free of medicament to provide a flow channel for the first motive fluid to the channel in the tip.

In another embodiment, the invention can include a control unit for modulating the supply of the first motive fluid and can include a conduit for supplying the first motive fluid from the control unit to the first passage in the handpiece. The control unit can further modulate the supply of the first and second fluids and can include a cable. The cable can include first and second conduits for supplying the first and second fluids from the control unit to the first and second passages in the handpiece, respectively. A second embodiment can include a circuit in the cable for supplying power to the handpiece.

In another embodiment, a medicament can be dispensed by connecting the cartridge containing the unit dose of medicament to a source of a motive fluid and supplying the motive fluid to displace the medicament from the reservoir through the channel in the tip onto a dental surface.

In another embodiment, a method of dispensing medicament can further comprise inserting the cartridge having the unit dose of medicament into the handpiece and supplying the first motive fluid to the reservoir to dispense the medicament from the reservoir through the channel in the tip.

In another embodiment, the unit dosage can be concentrated and the can further comprise mixing the medicament with the first fluid wherein the dispensed medicament is diluted.

In another embodiment, a method of dispensing medicament can further comprise a reservoir containing a plunger between the medicament and the first port, where the first fluid can push the plunger to displace the medicament from the reservoir.

In another embodiment, a method of dispensing medicament can comprise the steps of inserting the cartridge containing the unit dosage of medicament into the handpiece, supplying the second fluid through the flow channel to the mixing element, supplying the first fluid to the reservoir to displace medicament and form a first mixture of the first fluid and the medicament, mixing the second fluid with the first mixture to form a second mixture of the medicament and the first and second fluids, and discharging the second mixture from the tip.

In another embodiment, a method of dispensing medicament can comprise the steps of modulating the supply of the first and second fluids to control a rate of the displacement of the medicament.

In another embodiment, a method for ultrasonically scaling teeth can comprise assembling the cartridge to the ultrasonic element and inserting the assembly into the handpiece, powering the ultrasonic element to scale a dental surface, and supplying the first fluid to the reservoir to dispense the medicament through the flow path in the ultrasonic element for discharge adjacent the tip.

In another embodiment, a system for dispensing medicament with single-use cartridges can comprise having an inventory comprising a plurality of like cartridges, each having a reservoir containing a unit dose of medicament, and having a handpiece with a cavity for removably receiving one of the cartridges with a tip operably connected at a distal end of the cartridge projecting through an opening at a distal end of the handpiece. The handpiece can have a source of a first fluid in communication with a first passage in the handpiece, and a first port in the cartridge for connecting the first passage to the reservoir for supplying the first fluid to displace medicament from the reservoir through a channel in the tip.

In another embodiment, the inventory of cartridges can comprises a plurality of subsets of the cartridges wherein each subset comprises cartridges containing a different medicament from the other subsets. In another embodiment, a method of dispensing medicament can comprise the steps of selecting one of the cartridges from the inventory, inserting the cartridge having the unit dose of medicament into the handpiece, supplying the first fluid to the reservoir to dispense the medicament from the reservoir through the channel in the tip, removing the cartridge from the handpiece, and repeating the selection, insertion, and removal steps with a new cartridge from the inventory. This method can further comprise the step of sterilizing the handpiece prior to the repetition.

DETAILED DESCRIPTION

Figure 1:
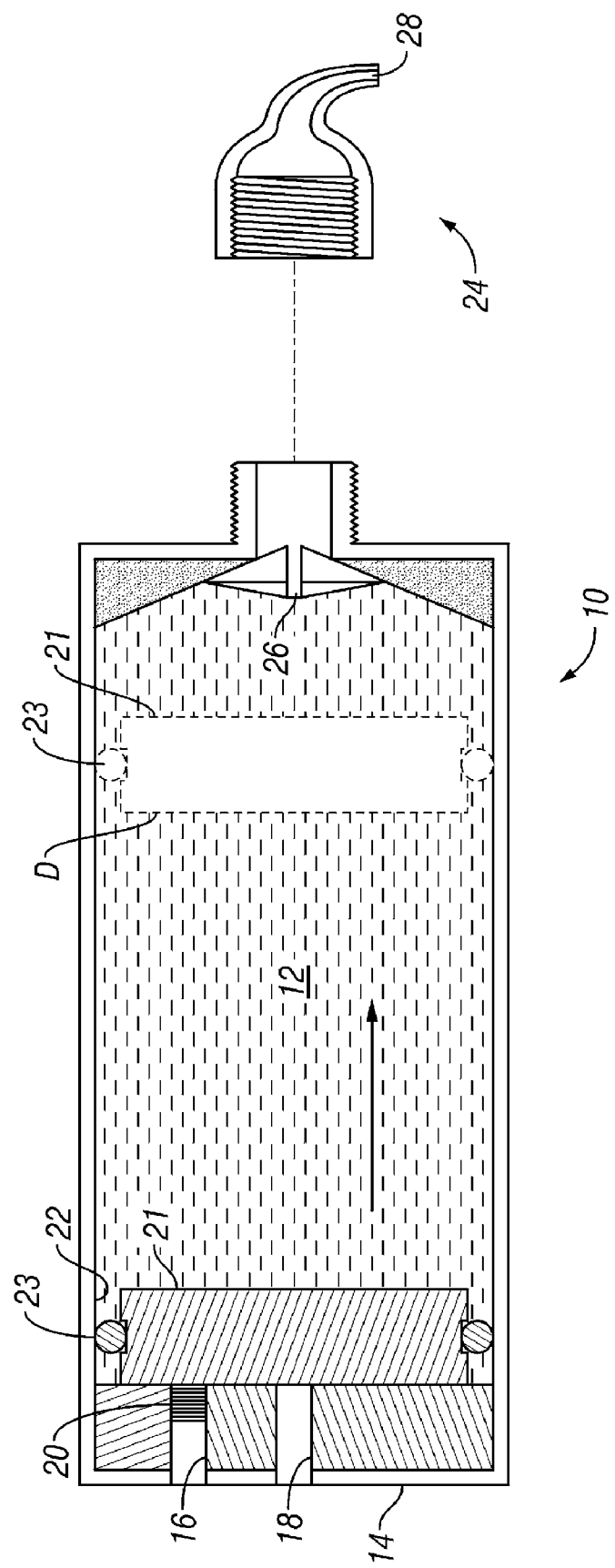
FIG. 1 is an exploded sectional view of a two port single use cartridge with a plunger shown in an initial and an advanced position (dashed lines) according to one embodiment of the invention.
Figure 2:
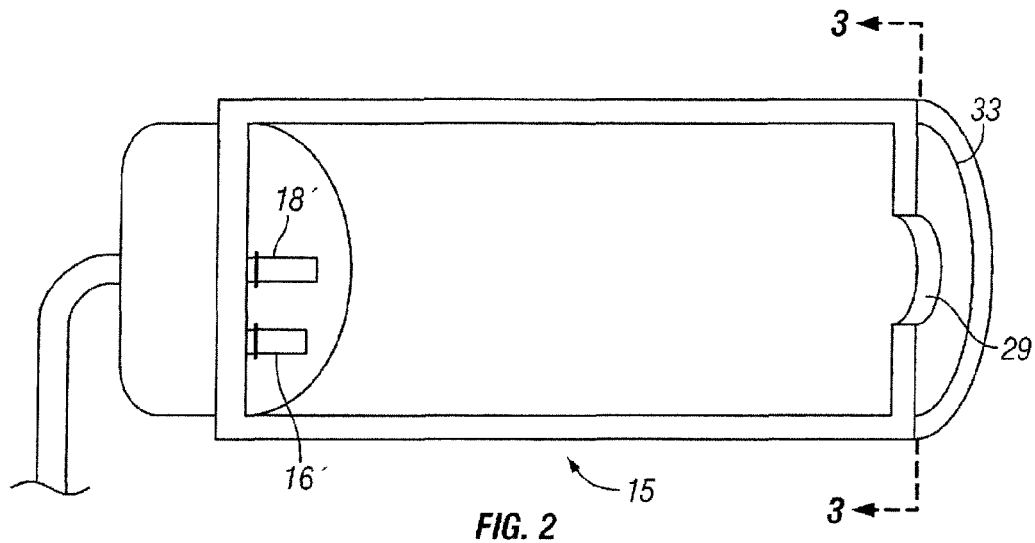
FIG. 2 is a perspective view of a handpiece that can be used with the cartridge of FIG. 1, according to one embodiment of the invention.

FIGS. 1-4, according to one embodiment, show a single use medicament delivery cartridge 10. The cartridge houses a reservoir 12 which contains medicament, preferably a unit dose for use in dental procedures. The volume of the unit dose can be adjusted depending on the size of the single use cartridge, the type of medicament and dosing requirements, the type of dental procedure, and the like. A proximal end 14 of the cartridge 10 can interlock the handpiece 15, as best seen in FIG. 2. A first cartridge port 16 and a second cartridge port 18 are provided at the proximal end to introduce fluids to the reservoir 12, such as, for example, air and water. In alternative embodiments, there can be a single cartridge port or more than two cartridge ports, depending on the number of different fluids or sources of fluids to be supplied.

In the embodiment illustrated, the cartridge port 16 can be blocked to prevent or inhibit fluid from flowing into the reservoir 12 by an obstruction such as a plug 20, and the port 18 can be open to allow fluid passage. Alternatively, the port 16 can be open and port 18 blocked, if a different motive fluid is desired for the particular medicament, or both ports 16 and 18 can be open to allow the use of dual motive fluids. The plug 20 can be a plug that is inserted or a plug that is molded into the single use cartridge. The plug 20 can be removable or permanent, e.g. formed as an integral part of the cartridge 10, or inserted when the cartridge 10 is filled with medicament through one of the ports 16,18 and/or the distal end at the tip attachment nozzle.

If used, a plunger 21 can be disposed in the single use cartridge 10 adjacent the proximal end between the port 18 and the medicament in reservoir 12 to prevent contact between fluid introduced through the port 18 and the medicament. The plunger 21 can sealably contact an inner wall 22 via O-ring seal 23 carried on a groove or channel at an outside diameter of the plunger 21. Alternatively, the plunger 21 can be a unitary or composite construction with a suitable perimeter seal that can be integral with the plunger. The plunger 21 can be made from a suitably rigid material(s) compatible for use with one side in contact with the motive fluid and the other side in contact with the particular medicament to be dispensed.

A tip 24 can be threadably or otherwise removably connected to the distal end of the single use cartridge 10 for directing the medicament discharge. A flow control orifice 26 can, if desired, be disposed in the cartridge 10 adjacent the tip 24 for limiting the flow of medicament. Orifice 26 can be sized for different tips, different fluid pressures, different types of medicament, different dosage delivery rates, and so on.

Medicament is dispensed by a dental professional or other operating personnel introducing the selected motive fluid such as water or air to one or both of ports 16,18. In the embodiment shown in FIG. 1 port 18 is open and port 16 is blocked, so the cartridge 20 is connected to the desired motive fluid via port 18. The motive fluid flows from the port 18 into the reservoir 12 to push the plunger 21, if present, and displace the medicament into a channel 28 for discharge from the distal end of the tip 24. FIG. 1 shows movement of the plunger 21 from an initial position adjacent the ports 15,16, toward the orifice 26 at D (show in dashed lines) as the medicament is displaced. If the plunger 21 is not used, the motive fluid can also mix with the medicament.

The first and second fluids can be any type of fluid, i.e. liquid or gas. Dental offices typically have office air and water supplies, for example, which can be used as the motive fluid in this invention, but any desired gas, liquid or similar fluid or mixture of fluids can be used. For convenience and clarity, the invention is illustrated herein with air and water as motive fluids by way of example and not limitation.

FIGS. 1-4 show male handpiece ports 16',18' that extend into the female ports 16,18 in the proximal end 14 of the cartridge 10, but the ports 16,18 can be male and ports 16',18' female, or one of the ports 16,18 could be female and the other male and the corresponding ports 16',18' would be male and female. Moreover, the ports are not limited to male and female ports, and can be any connective means known to those skilled in the art. The alignment of cartridge ports 16,18 and handpiece ports 16',18' can facilitate an interlocking registration between the cartridge 10 and handpiece 15 to ensure the cartridge 10 is positioned and aligned appropriately in the handpiece 15 so that the desired motive fluids are supplied to the appropriate ports 16,18. The registration can alternatively or additionally be effected by using ports of different sizes, e.g. relatively larger ports 16,16' for water and relatively smaller ports 18,18' for air, or by asymmetric positioning of the ports, e.g. axially aligned ports 16,16' for water and offset ports 18,18' for air. Similarly, a registration pin(s) and corresponding slot(s) can be used between the handpiece and the cartridge for alignment purposes.

The cartridge ports 16,18 can also be selectively blocked or open so as to allow the desired motive fluid into the reservoir and/or to push the plunger, as may be required for different medicaments or procedures. By configuring the cartridge ports 16,18 for the particular medicament, e.g. in conjunction with a standardized controller (see below) and handpiece, the cartridge can automatically provide for the use of the appropriate motive fluid without requiring the operator to manually select the fluid. By blocking one of the ports 16, 18, the motive fluid can be selected to match the requirements of the medicament. For example where a medicament is to be mixed with water, the air port can be blocked; or where air is the desired motive fluid for the appropriate dispensing rate, the water port can be blocked.

A source of a first fluid is connected to a first port 16' in the handpiece 15, and a source of a second fluid to a second port 18'. These ports can connect to the fluid supply through channels formed in a proximal end of the handpiece 15, e.g. by extending supply tubing or other conduit from an attachment cable through the proximal end of the handpiece to terminate at the respective ports 16',18'. In one embodiment the termini of the supply tubing can conveniently be formed into the ports 16',18'.

Connecting the single use cartridge 10 and the handpiece 15 can connect or be effected by engaging the male handpiece port 16' to female cartridge port 16, and the male handpiece port 18' to cartridge port 18, at the proximal end 14 of the cartridge 10. The cartridge ports 16,18 can form a fluid-tight seal to the handpiece ports 16',18' by an o-ring seal, friction seal, or other conventional sealing means.

Figure 3:
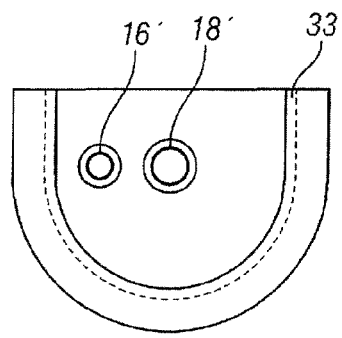
FIG. 3 is an end view of the handpiece of FIG. 2, as seen along the lines 3-3.
Figure 4:
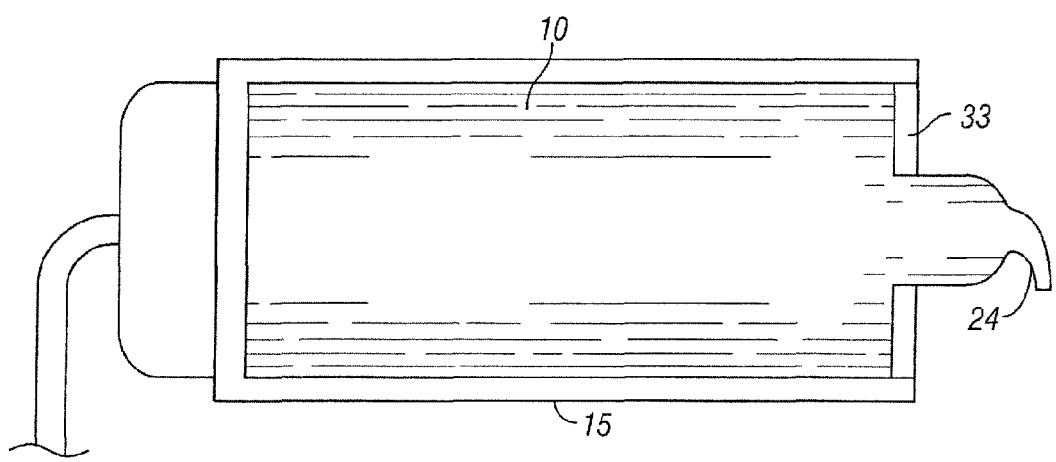
FIG. 4 is a perspective view of the assembled cartridge and handpiece of FIGS. 1-3.

The distal view of the handpiece 15 in FIG. 3 shows an opening 29 at the distal end that allows the tip 24 to project from the distal end of the handpiece 15. The opening 29 can include a peripheral lip 33 to facilitate retention of the cartridge 10 in the handpiece 15, and can have a profile matching that of the distal end of the cartridge 15 to hold it tightly in place and inhibit lateral movement during administration of the medicament by the dental practitioner. Alternatively, the handpiece 15 can have a hinged body (not shown) that surrounds the single use cartridge with an aperture for exposing the tip.

Handpiece 15 in FIG. 2 is shown as having a cavity for receiving the cartridge 10 (see FIG. 4), but the cartridge 10 can be used independently of the handpiece 15. For use without a handpiece, the user can hold the single use cartridge 10 itself, and the source(s) of motive fluid can be removably attached directly to one or both of the ports 16,18 on the cartridge using connective means known in the art, such as, for example, a slip fit, threaded connection, or the like.

The distal end of the handpiece 15 can have a peripheral lip 33 adjacent the opening 29 for engaging the distal end of the cartridge 10, e.g. at an edge of the outer profile. The lip 33 can help retain the cartridge 10 connected to the handpiece 15 (see FIG. 4) through an overlap or friction fit with the distal end of the cartridge 10, or another connective means known in the art to prevent the cartridge 10 from separating from and/or moving with respect to the handpiece 15 in use. The ports 16,18 and 16',18' can provide a similar retention function at the proximal end of the cartridge 10. One or both the proximal and distal ends of the cartridge 10 or preferably the handpiece 15 can provide spring biasing in a conventional manner to facilitate insertion and removal of the cartridge 10 to and from the handpiece 15.

In use, the dental professional or other operating personnel can receive a supply of a plurality of cartridges 10 each filled with a unit dose of medicament sufficient for a single use. An inventory of cartridges with different medicaments or different dosages for different procedures can also be maintained on hand. Each cartridge 10 can be individually packaged with or without tip 24 and sterilized, e.g. by radiation, gas (ethylene oxide) permeation, or the like. The handpiece 15 can be sterilized by autoclaving, or provided as a disposable, pre-sterilized single use device. One of the cartridges 15 containing the appropriate medicament for the intended procedure can be selected from the inventor, assembled into the handpiece 15, and connected to a suitable source of air and/or water. The dental practitioner can then introduce air and/or water into the reservoir 12 of cartridge 10. The fluid acts directly on the medicament and optionally mixes with the medicament, or against the plunger 21, displacing medicament or a fluid and medicament mixture through channel 28 in the tip 24 to the dental surface or tissue of the patient. After the procedure is completed or the medicament exhausted, the spent cartridge 10 can be removed from the handpiece 15 for disposal or return to the supplier for refilling, the handpiece 15 autoclaved or otherwise sterilized, or replaced with another handpiece 15, and a new cartridge 10 installed for the next application procedure or patient. The handpiece 15 can be constructed of a material suitable for use in an autoclave or other sterilization equipment if it is not disposable.

The tip 24 can be removable, so one can use a disposable tip 24, autoclave or otherwise sterilize the tip 24 for re-use, use different types or sizes of tips 24 for different procedures or application requirements, or change the tip 24 during the procedure, or the like. The tip 24 can also be built integrally into the cartridge 10 and/or supplied with the cartridge 10, either separate or pre-assembled to the cartridge 10. The single use cartridge 10 can be manufactured of any material or materials that are suitable for use in containing medicament.

The medicament can be placed in the reservoir during manufacture of the cartridge or later. The medicament can conveniently be injected into the ports 16,18 or the tip connection nozzle. Alternatively, where the plunger 21 is used, the plunger 21 can be positioned distally adjacent to the tip 24, the tip 24 immersed in the medicament, and the plunger 21 retracted to draw in the medicament through the tip 24 by temporarily connecting one or both of ports 16, 18 to a vacuum source.

The cartridge 10 can be transparent or translucent so that the volume of remaining medicament can be determined visually. The reservoir can contain a single medicament, or a mixture of medicaments, such as, for example, dental preparations, polishing compounds, bleaching or whitening agents, cleansers, anesthetics, analgesics, antiseptics, dyes, adhesives, solvents, astringents, sealants, fluoridation agents, impression materials, combinations thereof, or the like. Medical, veterinarian and other medicaments can also be dispensed in the cartridge 10, it being understood that dental use is merely exemplary for illustrative purposes and can have the advantage that dental practitioner offices are typically provided with instrument air and water supplies that can be readily used as the motive fluid. The medicament can be in any suitable form, such as, for example, liquid, solution, emulsion, dispersion, gel, paste, slurry, foam, powder, or the like.

The cartridge 10 can be for a single use. The single use cartridge 10 can be replaced quickly during a dental procedure or after the procedure. If the tip 24 is removable, different styles and sizes of tips can be interchangeably used with the cartridge 10. The ease of cartridge replacement can allow for multiple cartridge changes during a procedure for a single treatment modality as well as mixed treatment modalities such as using more than one medicament sequentially, for example dispensing fluoride gel from one cartridge followed by tooth surface sealing using another cartridge, or the like. For use of different cartridges with the same patient, it ma not be necessary to sterilize the handpiece, and thus the same handpiece could be used for the different procedures.

The cartridge can be supplied in a sealed, sterile package. The sealed package can inhibit moisture from entering the reservoir, and can optionally include a desiccant. The single use cartridge 10 can have a disposable cap to seal the openings (at ports 16,18, at the tip 24 or corresponding attachment point) before use, or the openings can be sealed with foil or other protective covering or membrane that can be punctured before use or by insertion of the cartridge 10 into the handpiece 15, e.g. with the male ports 16',18' piercing a covering over the female ports 16,18. A removable cap on the entry and exit ports of the single use cartridge 10 can retain the medicament in the reservoir 12 before use. The packaging of the cartridge 10 can have a complementary geometry to seal the entry and exit ports of the cartridge to seal the medicament in the reservoir 12 before use.

By providing the plunger 21 or other impermeable membrane between the medicament and the ports 16,18, medicament can be dispensed without the addition and/or mixing of motive fluid. Instead, the plunger 21 is moved longitudinally as shown in FIG. 1 or expanded by the entry of the fluid to displace medicament from the reservoir 12. Some medicaments can be of a two part or three part mixture, etc. The single use cartridge 10 can dispense multipart medicaments with or without mixing with motive fluid, for example, by partitioning the reservoir 12 into compartments for each medicament part and independently supplying motive fluid to each compartment to displace the medicaments into the tip 24, either simultaneously with optional mixing in the tip 24 and/or sequentially.

Alternatively, a plurality of stackable cartridges, each containing different medicaments can be used, where the stack has an overall length corresponding to the length of the cavity in the handpiece. The proximal cartridge can have a proximal end that selectively registers with the handpiece and a distal end that selectively registers with the proximal end of the distal cartridge to pass medicament and/or fluid into the distal cartridge; and the distal cartridge can have a distal end with a tip. In this manner a medicament in a first stackable cartridge can react with another medicament in another cartridge to form an active medicament to be dispensed. As one non-limiting example, the proximal cartridge can be plunger operated to discharge a relatively stable medicament directly into the reservoir of the distal cartridge where it reacts with the relatively stable medicament in the reservoir of the distal cartridge and thereby forms an unstable reaction product that is dispensed from the tip of the distal cartridge. The cartridge stack elements can be stored pre-measured until ready for use, and the registration indicia at the ends of the cartridge stack elements can prevent improper assembly in the handpiece.

Figure 5:
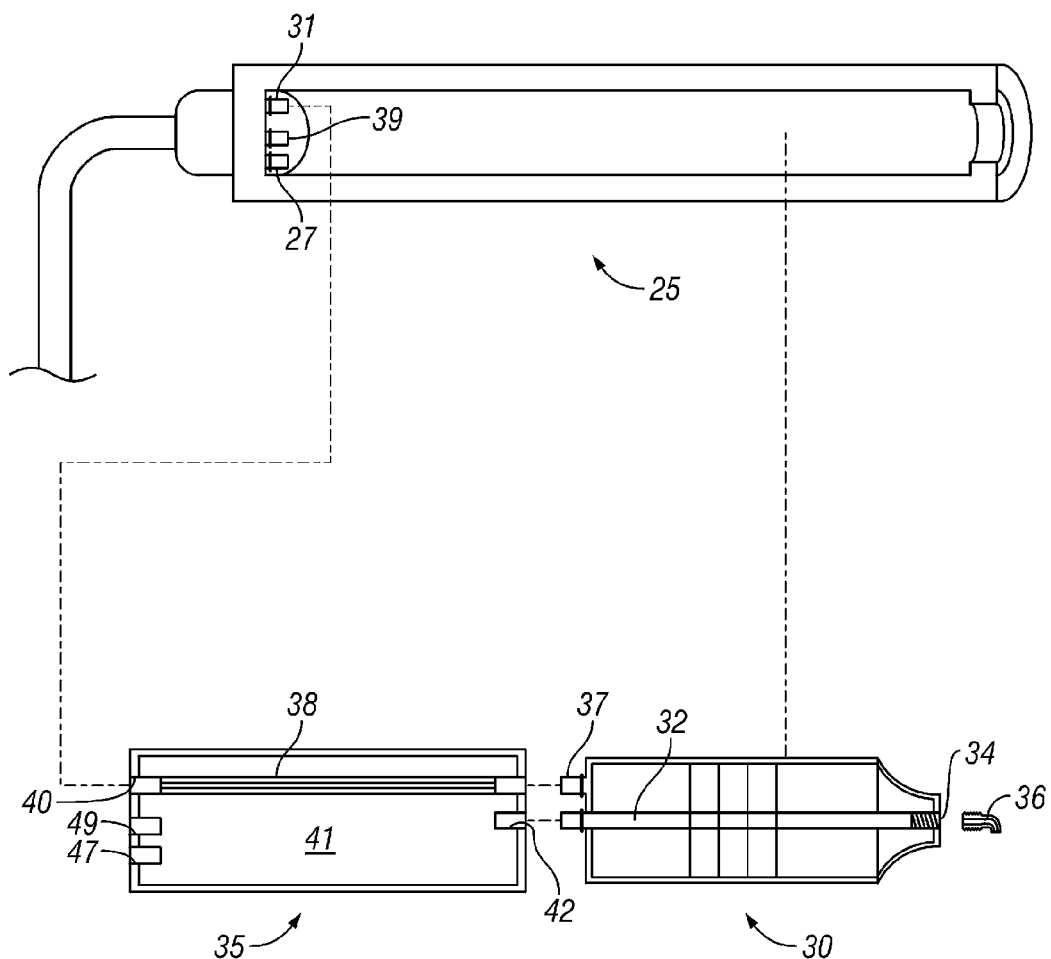
FIG. 5 is an exploded perspective view of a single-use cartridge used in an assembly with an ultrasonic element in a handpiece, according to one embodiment of the invention.

In FIG. 5, according to one embodiment, an assembly of a single use medicament cartridge 35 and an ultrasonic vibratory element 30 can be used in a handpiece 25. The ultrasonic element 30 can be piezoelectric, magnetostrictive, ferroelectric, or any other type of ultrasonic element known in the art. The ultrasonic element can also be a piezoelectric ceramic element or any other piezoelectric element known in the art.

The single use cartridge 35 in this embodiment is sized lengthwise to fit into the handpiece 25 when assembled with the ultrasonic element 30. In this manner, the same handpiece 25 can be used, if desired, in both ultrasonic and non-ultrasonic applications. The cartridge used in the non-ultrasonic application can have a length that equals the total length of the cartridge 28 and element 30, or a spacer or dummy cartridge (with appropriate flow through passages for the supplied fluid (s)) can be used to make up the required length.

In FIG. 5, the handpiece port 39 can supply a first motive fluid, the port 27 a second motive or mixing fluid, and handpiece connector 31 can provide an electrical or other power source connection(s) to the cartridge 35. More or fewer ports and/or power connections can be used if desired.

The single use medicament cartridge 28 can have ports 47,49 for receiving fluid from handpiece ports 27,29, respectively, to allow the user to supply water, air, a combination of water and air (simultaneously or sequentially), or similar motive and/or mixing fluid(s).

The medicament cartridge contains a circuit 38 through the cartridge 35 for supplying power from the handpiece power connector 31 to an electrical connection 37 with ultrasonic element 30, which can include a male/female plug-in type connector, for example, with corresponding pins and sockets. The circuit 38 can include a fluid impervious sheath surrounding the wiring, which can also be coated, or in another embodiment a conduit can be positioned or molded into the cartridge to allow the circuit to pass through the cartridge while separating the circuit from the medicament and/or motive fluid(s).

The ultrasonic element 30 can have a flow path 32 for fluid flow from the reservoir 41 of the single use cartridge 35 to the screw-in tip 36. Although the end of the flow path 32 is shown with a threaded port 34, the tip can be screw-in, snap-in, snap-on, integrally formed on the ultrasonic element, or any other conventional tip connecting means known in the art. The flow path 32 connects to the reservoir 41 of cartridge 35 at a port 42 on the distal end of the cartridge 35. Port 42 can be male as shown, or female.

In use, the dental professional connects the ultrasonic element 30 to the cartridge 35 which are then inserted as an assembly into the handpiece 25. The dental professional then powers the ultrasonic element 30 to scale a dental surface using techniques and methodology well known in the art, but with the fluid supply and medicament dispensing features of the present invention. A medicament or mixture of medicaments can be dispensed before, during, or after the scaling. For example, an antimicrobial rinse can be applied by supplying air and/or water into the reservoir through a respective port. The fluid can be controllably flowed into the single use cartridge 35 by an on-off and/or adjustable rate controller. Similarly, the dental professional can install a "dummy" cartridge 35 with no medicament in the reservoir 41 that allows fluid to flow through the cartridge 35 to the ultrasonic element 30, for procedures that do not require medicament but require air, water or other fluid(s) for operation, e.g. water for irrigation and cooling.

The ultrasonic element 30 can be made of a material that is suitable for use in an autoclave or other means of sterilization. The ultrasonic element 30 and cartridge 35 assembly can be removed as an assembly and a medicament cartridge only can be connected to the handpiece 25. The cartridges can have a port or multiple ports blocked off if they are not needed. The cartridge 35 can also include a plunger disposed adjacent the proximal end between the ports 47,49 and the medicament in reservoir 41 to prevent contact between fluid introduced through the ports 47,49 and the medicament, similar to that shown in FIGS. 1-4. The plunger can have an aperture that allows the circuit 38 to sealably pass through the plunger as the plunger moves to displace medicament.

Figure 6:
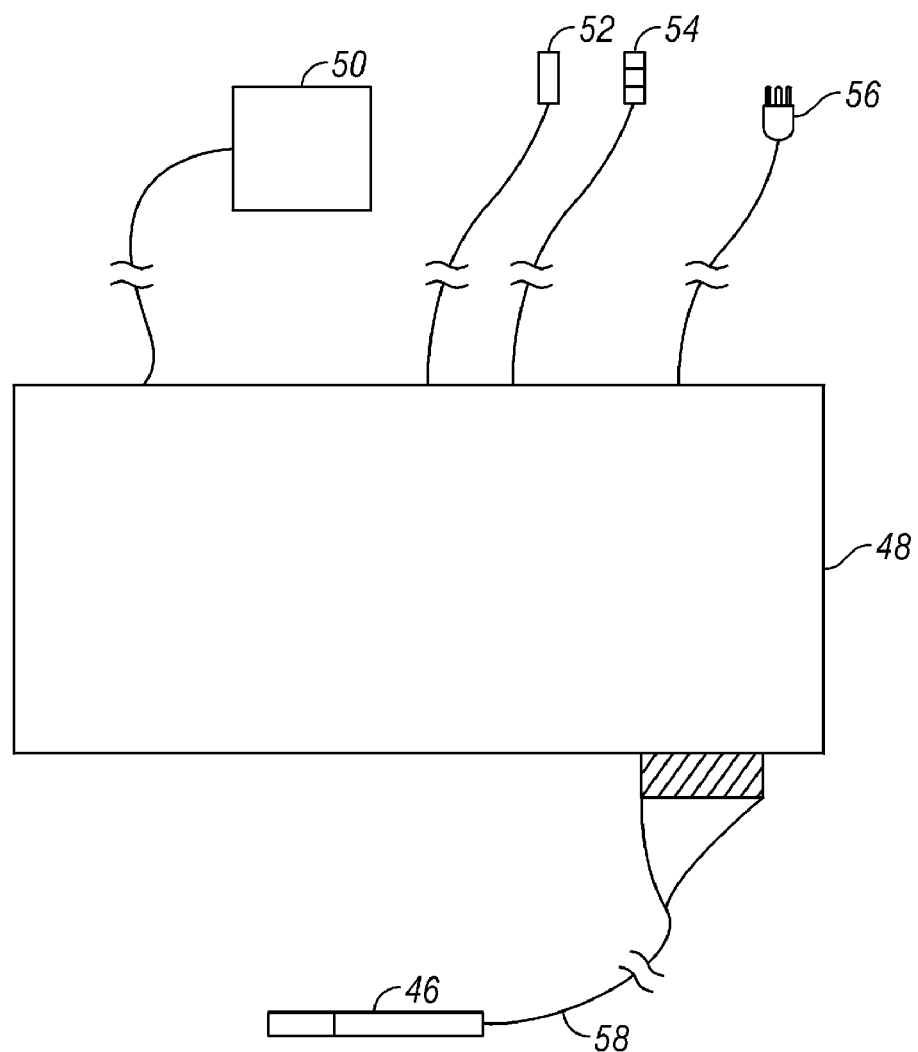
FIG. 6 is a schematic view of a control and fluid/power supply system for the handpiece and cartridge assembly, according to one embodiment of the invention.

In FIG. 6, according to one embodiment, a control unit 48 can connect to a handpiece 46, a cable 58, and have a foot control switch 50 for controlling the supply of motive fluid and/or power. The cable 58 can include one or more fluid supply conduits for air and/or water, for example, and an electrical line or lines for supplying power, if required. Alternatively, there can be more than one cable 58 to the handpiece 46 carrying separate fluid conduits or power lines or any combination thereof, optionally including a sheath or other conventional cable covering, or the cable 58 can comprise an unsheathed conduit or tubing.

The control unit 48 can be supplied with motive fluids 52, 54, and power 56. The control unit 48 can regulate the flow of air or water using conventional valves (not shown) operated by the foot switch 50 or via settings on the control unit 48, which can be automatic or manual. Power can be regulated by a potentiometer, for example, in either the footswitch 50 or the control unit 48 such as with an adjustable dial. Fluid and power can include an on-off controller, a modulating or regulating controller, or both. For example, the fluid flow rate or power setting can be set manually or automatically at the control unit 48 and turned on or off via the footswitch 50. The footswitch 50 can also included potentiometer(s) that control the rate of fluid supply, e.g. by means of a valve(s), regulation of the fluid supply pressure, or the like. Further, a programmable logic controller and/or step motor can be used to automatically sequence the fluid(s) and/or power supply for a particular procedure.

Although FIG. 6 shows a separate control unit 48 by way of illustration for the sake of clarity and convenience, the control unit 48 or any part thereof could be integrated with the handpiece. Furthermore, a separate control unit could be provided for each function of the handpiece.

Figure 7:
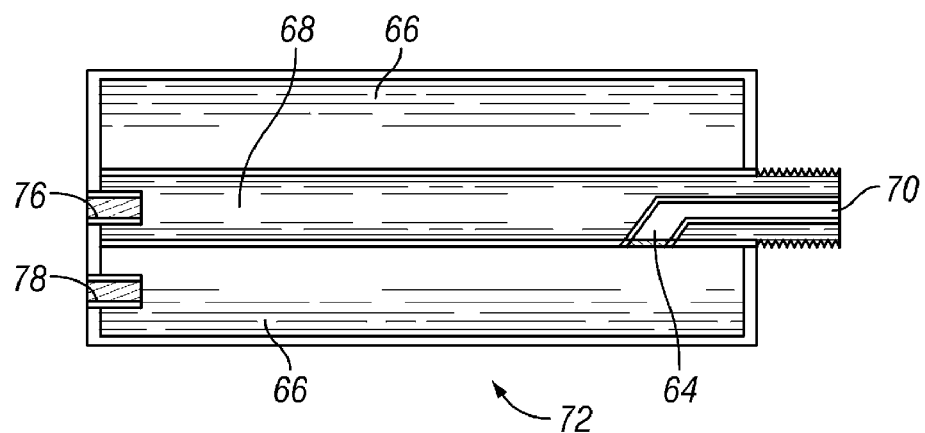
FIG. 7 is a perspective view of a two port cartridge with a mixing element and a screw-on tip according to one embodiment of the invention.

In FIG. 7, according to one embodiment, there is shown a cartridge system that can be used for polishing teeth with sodium bicarbonate particles in a spray mixture of air and water. The cartridge 72 can have a mixing element 70 including inner and outer concentric tubes 64,68. After connecting the cartridge 72 to a handpiece 15 (see FIG. 2), water is supplied into port 76 and air is supplied into port 78. Water flows from port 76 into tube 68 and directly to the distal end of the cartridge 72 through the annulus in mixing element 70 around the central tube 64. Air enters through port 78 into the reservoir 66, entraining sodium bicarbonate powder or other abrasive particles, thence flowing into mixing element 70 via inner tube 64 in the tube 68, where it is introduced into the annular water stream and the mixture discharged at the distal end of the cartridge 72.

In use, a dental professional or other operating personnel can insert a single use medicament cartridge 72 into handpiece 15 (FIG. 2). Water and air can be simultaneously supplied to ports 76 and 78, respectively. The air can flow into the reservoir 66, form a mixture of air and sodium bicarbonate for pneumatic transport into the mixing element 70 via air tube 64. The water flows through the tube 68 to the mixing element 70 where a mixture of air, water and abrasive particles can be formed in the tip. The water, air, and sodium bicarbonate mixture can be discharged in a forceful high velocity spray directed using the tip onto a tooth or other dental surface to remove calculus, tartar or other foreign matter, for tooth surface polishing. The powder can be maintained in the reservoir of the cartridge 72 prior to use as a dry, non-clumping, pneumatically conveyable powder. The single-use cartridge in this embodiment thus avoids the prior art problems associated with water absorption by large dispensing reservoirs of powder and the concomitant clumping of the powder and clogging of supply lines.

The tubes 64, 68 of mixing element 70 can be varied in size to control the mixing rate of the medicament and/or the volume of the discharged mixture. Similarly, the flow rates of the air and water can be varied to adjust the volume or the relative composition of the polishing spray. Alternatively, the mixing element 70 is not limited to concentric tubes, and can be, for example, a mixing nozzle, an eductor, or another suitable mixing element known in the art. Furthermore, tube 68 can be located within or adjacent the cartridge wall and need not be centrally disposed through the cartridge provided that the tube 68 provides a flow channel to supply water to the mixing element 70.

While the invention has been described with respect to a limited number of embodiments, those skilled in the art will appreciate numerous modifications and variations therefrom. It is intended that the appended claims cover all such modifications and variations as fall within the true spirit and scope of the invention.

What is claimed is:

1. A delivery device for medicament, comprising:
    a cartridge housing a reservoir containing a unit dose of medicament;
    a handpiece with a cavity removably receiving the cartridge, the handpiece including a retaining lip at a distal end thereof facilitating retention of the cartridge within the cavity;
    an ultrasonic element disposed in the handpiece;
    an ultrasonic tip in fluid communication with a distal end of the cartridge projecting through an opening at the distal end of the handpiece, the ultrasonic element being disposed between the distal end of the cartridge and the ultrasonic tip;
    a source of a first motive fluid in fluid communication with a first passage in the handpiece;
    a first port in the cartridge for connecting the first passage to the reservoir for supplying the first motive fluid to displace medicament from the reservoir though a channel in the ultrasonic tip;
    a flow path in the ultrasonic element in fluid communication with the reservoir and the channel in the ultrasonic tip; and
    an electrical circuit through the cartridge for supplying power from an electrical connection in the handpiece to an electrical connection in the ultrasonic element.

2. The delivery device of claim 1 wherein the cartridge is essentially free of medicament to provide a flow channel for the first motive fluid to the ultrasonic tip.

3. The delivery device of claim 1 further comprising a source of a second motive fluid in communication with a second passage in the handpiece; and a second port in the handpiece for connection to the second passage and a control unit and a cable from the control unit to the handpiece wherein the cable includes first and second conduits for supplying the respective first and second motive fluids to the respective first and second passages, and a circuit for supplying power to the electrical connection in the handpiece.

4. A method for ultrasonically scaling teeth with the delivery device of claim 1 comprising the steps of:
    assembling the cartridge to the ultrasonic element and inserting the assembly into the handpiece;
    powering the ultrasonic element to scale a dental surface; and
    supplying the first motive fluid to the reservoir to dispense the medicament through the flow path in the ultrasonic element for discharge adjacent the ultrasonic tip.

5. A delivery device for medicament, comprising:
    a cartridge housing a reservoir containing a unit dose of medicament;
    a handpiece with a cavity removably receiving the cartridge;
    a tip in fluid communication with a distal end of the cartridge projecting through an opening at a distal end of the handpiece;
    a source of a first motive fluid in communication with a first passage in the handpiece; and
    a first port in the cartridge for connecting the first passage to the reservoir for supplying the first motive fluid to displace medicament from the reservoir though a channel in the tip;
    an ultrasonic element disposed between the distal end of the cartridge and the tip;
    a flow path in the ultrasonic element in fluid communication with the reservoir and the channel in the tip; and
    an electrical circuit through the cartridge for supplying power from an electrical connection in the handpiece to an electrical connection in the ultrasonic element.

\* \* \* \* \*